United States Patent [19]

Nakano et al.

[11] Patent Number: 5,419,828
[45] Date of Patent: May 30, 1995

[54] AIR FUEL RATIO DETECTING APPARATUS AND METHOD FOR MANUFACTURING THEREOF

[75] Inventors: Syuichi Nakano, Kariya; Tomio Sugiyama, Nagoya; Tomoji Fukaya, Kariya; Masatoshi Suzuki, Nagoya, all of Japan

[73] Assignee: Nippondenso Co., Ltd., Kariya, Japan

[21] Appl. No.: 299,058

[22] Filed: Aug. 31, 1994

[30] Foreign Application Priority Data

Aug. 31, 1993 [JP] Japan .................................. 5-240361
Aug. 3, 1994 [JP] Japan .................................. 6-182158

[51] Int. Cl.$^6$ .............................................. G01N 27/26
[52] U.S. Cl. ................................... 204/425; 204/426; 204/429
[58] Field of Search ............... 204/425, 426, 428, 429, 204/427, 424

[56] References Cited

U.S. PATENT DOCUMENTS

| | | | |
|---|---|---|---|
| 4,282,080 | 8/1981 | Muller et al. | 204/425 |
| 4,356,065 | 10/1982 | Dietz | 204/425 |
| 5,169,513 | 12/1992 | Mase et al. | 204/425 |
| 5,288,389 | 2/1994 | Yamada et al. | 204/425 |

FOREIGN PATENT DOCUMENTS 61-186849 8/1986 Japan .

*Primary Examiner*—John Niebling
*Assistant Examiner*—Bruce F. Bell
*Attorney, Agent, or Firm*—Cushman, Darby & Cushman

[57] ABSTRACT

An air fuel ratio detecting apparatus by which a stable oxygen ion limit current may be obtained, including a working electrode and a gas diffusion resistance layer laminated in this order on a first surface of a solid electrolyte. An ambient air introduction duct and an electric heater are laminated in this order on a second surface of the electrolyte. The gas diffusion resistance layer is composed of a gas permeation layer and gas shield layer, which is provided on a surface of the gas diffusion resistance layer. Since the surface of the gas permeation layer is covered by the gas shield layer, the gas to be measured enters into the gas diffusion resistance layer from only side faces of gas diffusion resistance layer. A cell is preferably baked in a one-piece manner. A porosity of the gas permeation layer is in a preferable range of from about 2 to about 60%, a thickness of the gas permeation layer is preferably in a range of from about 5 to about 300 μm, and a porosity of the gas shield layer is preferably no more than 10%. Also, the periphery of the cell is preferably covered by a protective layer.

12 Claims, 8 Drawing Sheets

AIR FUEL RATIO DETECTING APPARATUS AND METHOD FOR MANUFACTURING THEREOF

BACKGROUND OF THE INVENTION

1. Field of the Invention

The present invention relates to an air fuel ratio detecting apparatus.

2. Description of Related Art

Similar air fuel ratio detecting apparatus are disclosed in Japanese Examined Patent Publication (Kokoku) No. 63-39852 and Japanese Patent Application Laid-Open (Kokai) No. 61-186849.

In the case of Japanese Examined Patent Publication No. 63-34852, a pair of electrodes are formed in a solid electrolyte made of oxygen ion conductive metal oxide, and a working electrode, which is to be exposed in a gas to be measured is covered with a gas diffusion resistance layer.

In the case of Japanese Patent Application Laid-Open No. 61-186849, a wall member is juxtaposed in parallel with spaces relative to a working electrode, which is to be exposed in the gas to be measured, of a pair of electrodes formed in solid electrolyte. A diffusion chamber into which the gas flow is restricted is formed between the wall member and the solid electrolyte.

In the former case, a diameter of fine pores in a gas diffusion resistance layer is a primary factor for determining the diffusion resistance limited to the oxygen contained in the gas to be measured. On the other hand, in the latter case, a gap dimension between the wall member and the solid electrolyte, and a distance from a tip end of a diffusion chamber to a surface of an end of the working electrode, are factors for determining the diffusion resistance restricted to the oxygen contained in the gas to be measured.

These air fuel ratio detecting sensors are used to forcibly pump oxygen contained in the gas to be measured from one electrode to the other electrode of the solid electrolyte by applying a constant voltage between the pair of electrodes, and to measure a limit current that occurs between electrodes under this condition.

The limit current is adversely affected by the diffusion resistance of the gas to be measured in the diffusion resistance layer or the diffusion chamber.

The conventional air fuel ratio detecting apparatus suffers from the following disadvantages. Namely, the former case suffers from the following disadvantage in the manufacturing quality of the gas diffusion resistance layer, making it difficult to obtain a stable and good characteristic. In a first method of manufacturing the gas diffusion resistance layer, ceramic power such as spinel is adhered in a plurality of layers by plasma welding. As shown in FIG. 9, in the gas diffusion resistance layer 91 made according to this method, an adhesion thickness $\delta$ is not constant and diameters of fine pores 911 for gas diffusion are not constant.

FIG. 9 shows a slight modification of the cell 90 of the conventional air fuel ratio detecting sensor according to the former case. Reference numeral 92 denotes a solid electrolyte, numeral 93 denotes a working electrode, numeral 94 denotes a reference electrode, reference numerals 95 and 951 denote an ambient air introduction duct and its vent hole, respectively, and numerals 96 and 961 denote an electric thermal heater and its heating elements respectively.

In FIG. 9, fine pores 911 are depicted like tunnel-shaped passages. However, the actual fine pores 911 are gaps formed between the ceramic particles 910 which form the diffusion resistance layer 91, as shown in FIG. 10. The exhaust gas 8 is diffused and permeated as indicated by the arrows in FIG. 10.

As described above, the thickness $\delta$ of the gas diffusion resistance layer 91 manufactured by plasma welding is not uniform, and in particular, the diameter of the fine pores varies remarkably. Accordingly, the diffusion resistance changes depending upon a position of the gas diffusion resistance layer and the amount of gas to be measured (exhaust gas) passing through the fine pores varies.

As a result, the limit current of the oxygen ion current will hardly be settled at a constant level to cause a detection error as shown by a curve in FIG. 7.

In order to improve such a defect, for example, it is necessary to make uniform and fine the diameter of the fine pores of the gas diffusion resistance layer 91. However, it is practically a manufacturing impossibility to satisfy this requirement without considerably increasing manufacturing time and cost. Also, it is possible to consider that the thickness $\delta$ of the gas diffusion resistance layer 91 imparts the diffusion resistance. However, in this case, an extremely large thickness is required, so that the diffusion resistance layer itself is large in size and overall cell is enlarged. Also, if the diffusion resistance layer is large in size, the heat capacitance of the resistance layer is enlarged. Accordingly, it is likely that the heat of the electric thermal heater 96 would be used mainly for the diffusion resistance layer, as a result of which it would be impossible to effectively heat the solid electrolyte 92 and low temperature activation of the solid electrolyte 92 by the heater 96 would be difficult to obtain.

The latter case has the structure as shown in FIG. 11. In the latter case, in order to obtain a good limit current characteristic, it is necessary to keep the gap d between the wall member 97 and the solid electrolyte 92 exactly in parallel. This requirement is difficult to satisfy, due to the manner in which the units is desired. The unit includes the wall member 97 that is held to the solid electrolyte in a cantilever manner.

On the other hand, it is possible to considerably increase the length L from the tip end of the diffusion chamber 98 to the end face of the working electrode 93. However, this enlarges the structure corresponding to the solid electrolyte.

SUMMARY OF THE INVENTION

In view of the foregoing defects inherent in conventional systems, an object of the present invention is to provide an air fuel detecting apparatus which may obtain a stable and constant oxygen ion limit current.

According to a preferred embodiment (first embodiment) of the invention, there is provided an air fuel ratio detecting apparatus that includes a solid electrolyte having a pair of electrodes with a surface and side faces of one of the pair of electrodes being covered by a gas diffusion resistance layer having a diffusion resistance limited to oxygen contained in gas to be measured. The apparatus includes a gas diffusion resistance layer formed on the surface of the pair of electrodes and over an area from one of the side faces of the first electrode to a part of a surface of the solid electrolyte at a predetermined distance. Also, a gas shield portion is formed on a surface of the gas diffusion resistance layer, except for the side faces thereof. An area corresponding to the gas permeation layer which together forms the predetermined distance between the side face of the gas diffusion resistance layer and the side face of the first electrode exhibits a diffusion resistance action limited to the oxygen contained in the gas. Due to the existence of the gas shield portion, the gas to be measured reaches the first electrodes through an interior of the gas diffusion resistance layer from the side face of the gas diffusion resistance layer.

According to another preferred embodiment (seventh embodiment) of the invention, there is provided an air fuel ratio detecting apparatus comprising a plate-like solid electrolyte having a first surface for exposure in a gas to be measured and a second surface to be exposed in ambient air, a working electrode formed on the first surface of the solid electrolyte, a reference electrode formed on the second surface of the solid electrolyte, an ambient air duct arranged on the second surface of the solid electrolyte for exposing the reference electrode to the ambient air, an the solid electrolyte, and a gas diffusion resistance layer formed on the first surface of the solid electrolyte for covering a surface and side faces of the working electrode, with a surface portion of the gas diffusion resistance layer being formed of dense material that prevents the gas to be measured from entering in a vertical direction of the working electrode but allows the gas to be measure to enter from the side faces perpendicular to the vertical direction.

A distance between the side faces of the gas diffusion resistance layer and the side faces of the working electrode is set as a factor for determining a diffusion resistance limited to oxygen contained in the gas to be measured.

The present invention is also directed towards a method for manufacturing the gas diffusion resistance layer, comprising the step of laminating and baking a porous gas permeable ceramic sheet and a dense gas shield type ceramic sheet to thereby form the gas diffusion resistance layer.

The present invention also includes the method for manufacturing the air fuel ratio detecting apparatus, comprising the following steps of printing the pair of electrodes on surfaces of a solid electrolyte sheet, laminating, on one surface of the solid electrolyte sheet, a porous gas permeable ceramic sheet as well as one of the pair of electrodes, further laminating a dense gas shield type ceramic sheet on the gas permeation type ceramic sheet, and forming the gas diffusion layer having no permeation characteristic to the gas at its surface, on the surface of the solid electrolyte including the surface of one of the electrodes through a baking process.

According to the first embodiment of the present invention, the gas to be measured reaches the electrode surface through the interior of the resistance layer from the side faces of the gas diffusion resistance layer. Then, the area corresponding to the predetermined distance from the side faces of the gas diffusion resistance layer and the side faces of the electrode exhibits the diffusion resistance action limited to the oxygen contained in the gas to be measured.

The amount of the diffused gas which reaches the electrode is determined by a thickness d of the gas diffusion resistance layer, a distance L between each side face of the gas diffusion resistance layer and each side face of the electrode, and a porosity of the gas diffusion resistance layer.

It should be noted that the above-described distance L, i.e., a gas introduction length may be determined as desired unlike the thickness d. The effect as a factor that exhibits the diffusion resistance action restricted to the oxygen contained in the gas to be measured by the thickness of the gas diffusion resistance layer is no longer large.

Accordingly, it is unnecessary to increase the thickness of the diffusion resistance layer, and it is possible to avoid enlargement of the overall structure caused by the increase of the thickness of the resistance layer. Also, since the gas diffusion resistance layer is present in the part corresponding to the distance L, it is unnecessary to increase the length L to an extremely large value.

Thus, it is possible to obtain the uniform and stable oxygen ion limit current.

According to the second embodiment, it is possible to provide a structure which may effectively introduce the ambient air into the reference electrode. As described in conjunction with the first embodiment of the invention, since it is unnecessary to increase the thickness of the gas diffusion resistance layer, it is possible to avoid increases in the thermal capacitance of the resistance layer, and there is no fear that the heat of the electric heater is removed by the resistance layer on a large scale. Accordingly, it is possible to provide a structure which effectively heats the solid electrolyte with the electric heater.

BRIEF DESCRIPTION OF THE DRAWINGS

Other objects, features, and characteristics of the present invention, as well as economies of manufacture and the functions of the related elements, will become apparent from consideration of the following detailed description, appended claims, and attached drawings, all of which form a part of this specification.

In the accompanying drawings.

DETAILED DESCRIPTION OF THE PREFERRED EMBODIMENTS

Figure 1:
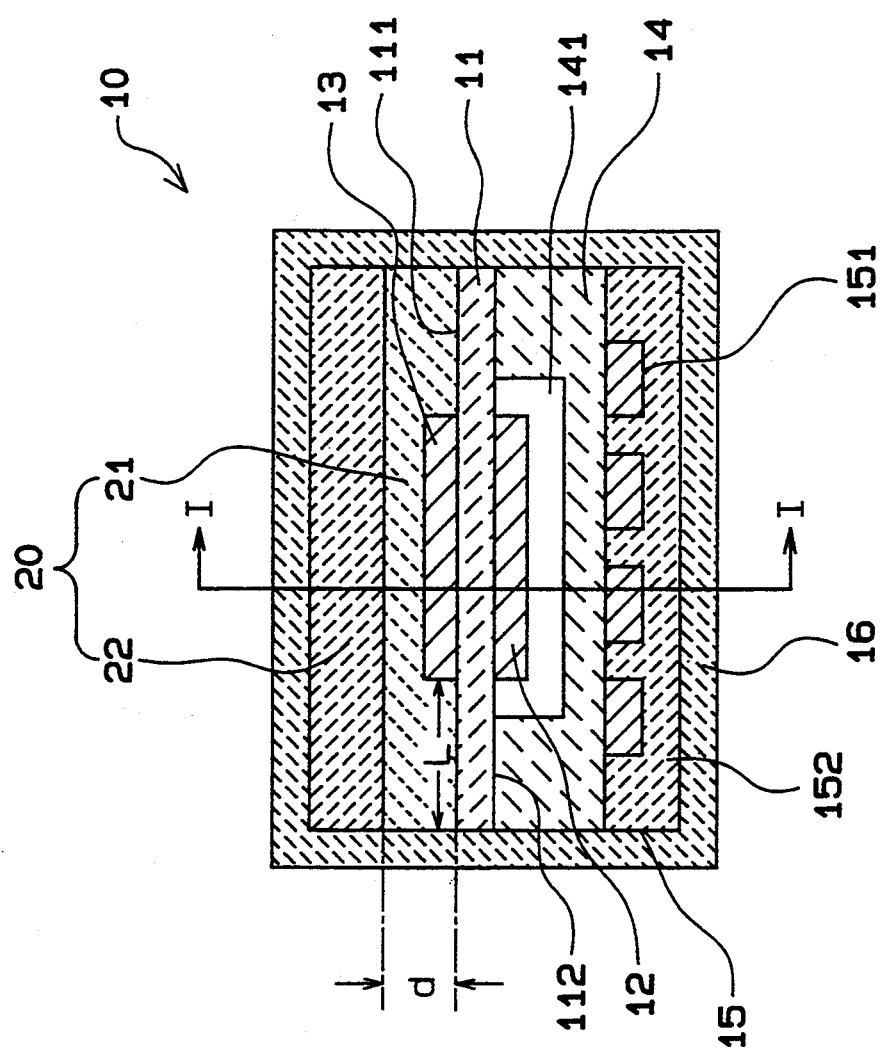
FIG. 1 is a cross-sectional view showing a cell of an air fuel ratio detecting apparatus according to a first embodiment.

An air fuel ratio detecting apparatus for a motorized vehicle will be described with reference to FIGS. 1 to 8.

As shown in FIGS. 1, 2, 3 and 4, an air fuel ratio detecting apparatus (FIG. 3) includes a solid electrolyte 11 having an oxygen ion conductivity, a working electrode 13 disposed on a first surface 111 of solid electrolyte 11 to be exposed in a gas to be measured, a reference electrode 12 disposed on a second surface 112 of solid electrolyte 11 to be exposed to ambient air, a gas diffusion resistance layer 20 provided on a surface opposite the working electrode 13, an ambient pressure introduction duct 14 provided on a surface opposite the reference electrode 12, and an electric thermal heater 15.

The gas diffusion resistance layer 20 made of heat resistant ceramics of a cell 10 is composed of two layers, i.e., a gas permeation layer 21 made of heat resistant ceramic disposed on the surface of the working electrode 13 and a gas shield layer 22 made of heat resistant ceramic disposed on the surface of the gas permeation layer 21 except for side walls thereof.

Cell 10 is integrally formed by baking the components 11 to 15 and 20 after these components have been stratified. The gas permeation layer 21 and gas shield layer 22 are simultaneously produced by baking a green sheet in the baking process of the cell 10.

Gas permeation layer 21 is porous, having a porosity in the range of from about 2% to about 60% (inclusive of upper and lower limits), preferably 30%, and a thickness in the range of from about 5 $\mu$m to about 300 $\mu$m (inclusive of upper and lower limits), preferably 10 $\mu$m.

The gas shield layer 22 is dense, having a porosity of 10% or less. The preferable range of the porosity of the gas permeation layer 21 is, as described above, in the range of 2 to 60%. If the lower limit is less than 2%, the permeability of the gas to be measured is too weak to obtain a sufficient detection output. If the upper limit of 60% is exceeded, the working electrode 13 would be aged and damaged for a short period of time by the gas to be measured, resulting in a short service life of the electrode 13.

The preferable range of the thickness of the gas permeation layer 21 falls in the range between 5 and 300 $\mu$m as described above. If the lower limit is less than 5 $\mu$m, it would be impossible to obtain sufficient detection output because the amount of gas to be measured and passing through the working electrode 13 from the side faces of the gas permeation layer 21 becomes very small. If the upper limit of 300 $\mu$m is exceeded, it would be impossible to obtain a sufficient responsibility.

On the other hand, if the porosity of the gas shield layer 22 exceeds 10%, the shield ability per unit thickness against the gas to be measured is lowered. In this case, it would be impossible to ensure a sufficient shield ability even if the thickness were increased. Also, the cell 10 is covered by a porous protective layer 16 for preventing the gas permeation layer 21 from clogging.

Figure 3:
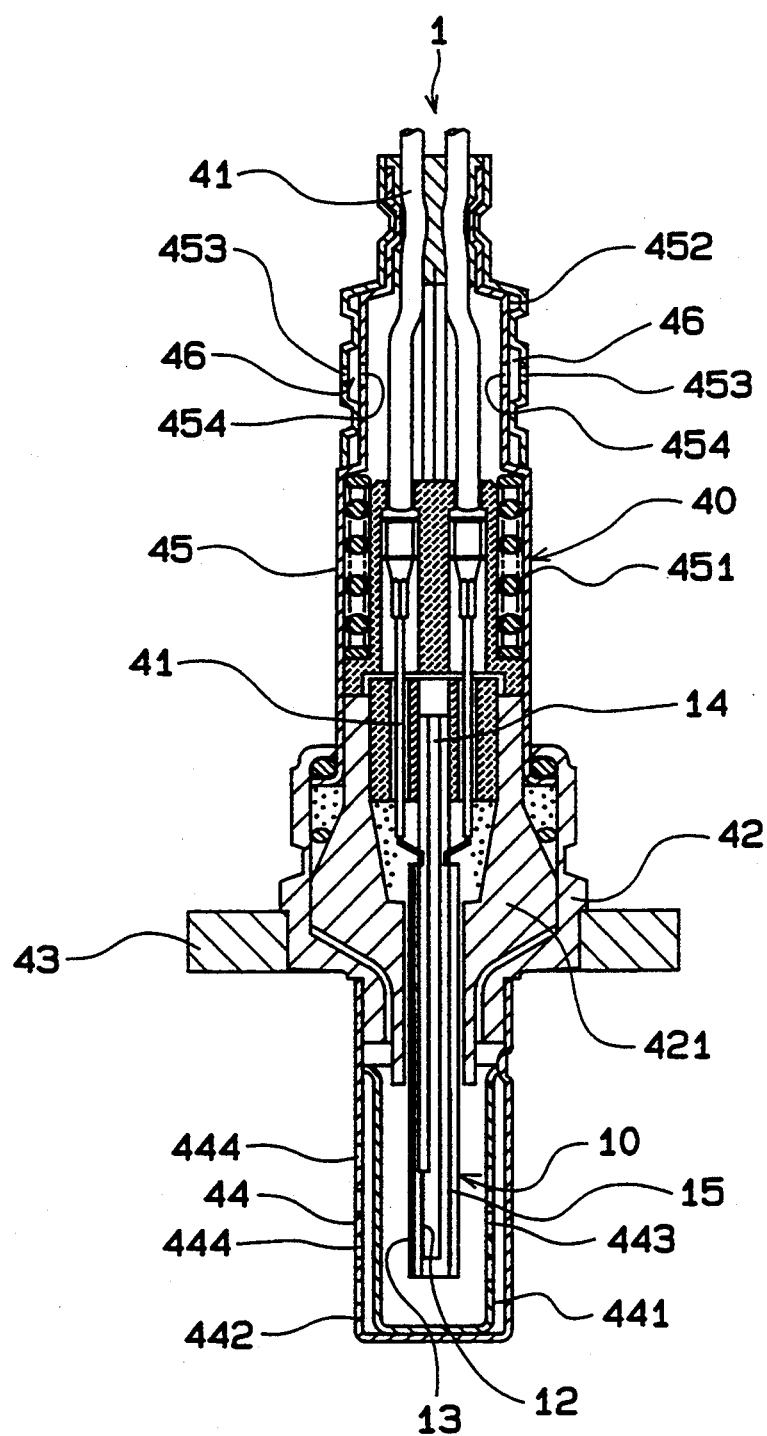
FIG. 3 is a cross-sectional view showing the air fuel ratio detecting apparatus according to the embodiment.

As shown in FIG. 3, the air fuel ratio detecting apparatus 1 includes the cell 10 incorporated into the interior of a housing 40, and a lead line 41 is connected to the cell 10. The housing 40 has a barrel portion 42 provided with a flange 43 at its central portion. An exhaust gas cover 44 to be inserted in an exhaust passage is provided below the barrel portion 42. An ambient air cover 45 to be exposed in the ambient air is provided above the barrel portion 42.

As shown in FIG. 3, the exhaust gas cover 44 has an exterior cover 442 and an interior cover 441 made of stainless steel. Discharge ports 443 and 444 are provided in the covers 441 and 442.

On the other hand, an ambient air cover 45 is provided with a main cover 451 mounted on the barrel portion 42 and a sub-cover 452 for covering a rear end portion of the main cover 451. Ambient air vent ports 453 and 454 are formed in the covers 451 and 452, respectively.

The above-described ambient air vent ports 453 and 454 are in fluid communication of the ambient air introduction duct 14 of the cell 10 to be described later. A water-protective water-repulsive filter 46 is inserted in between both the ambient air ports 453 and 454.

The detecting portion 10 is clamped by a dielectric member 421 and installed within the barrel portion 42.

Also, the lead line 41 connected to the detecting portion 10 is composed of a pair of signal lines for extracting the cell output and a pair of heater lines for supplying the electric heater 15 with electric power.

Figure 2:
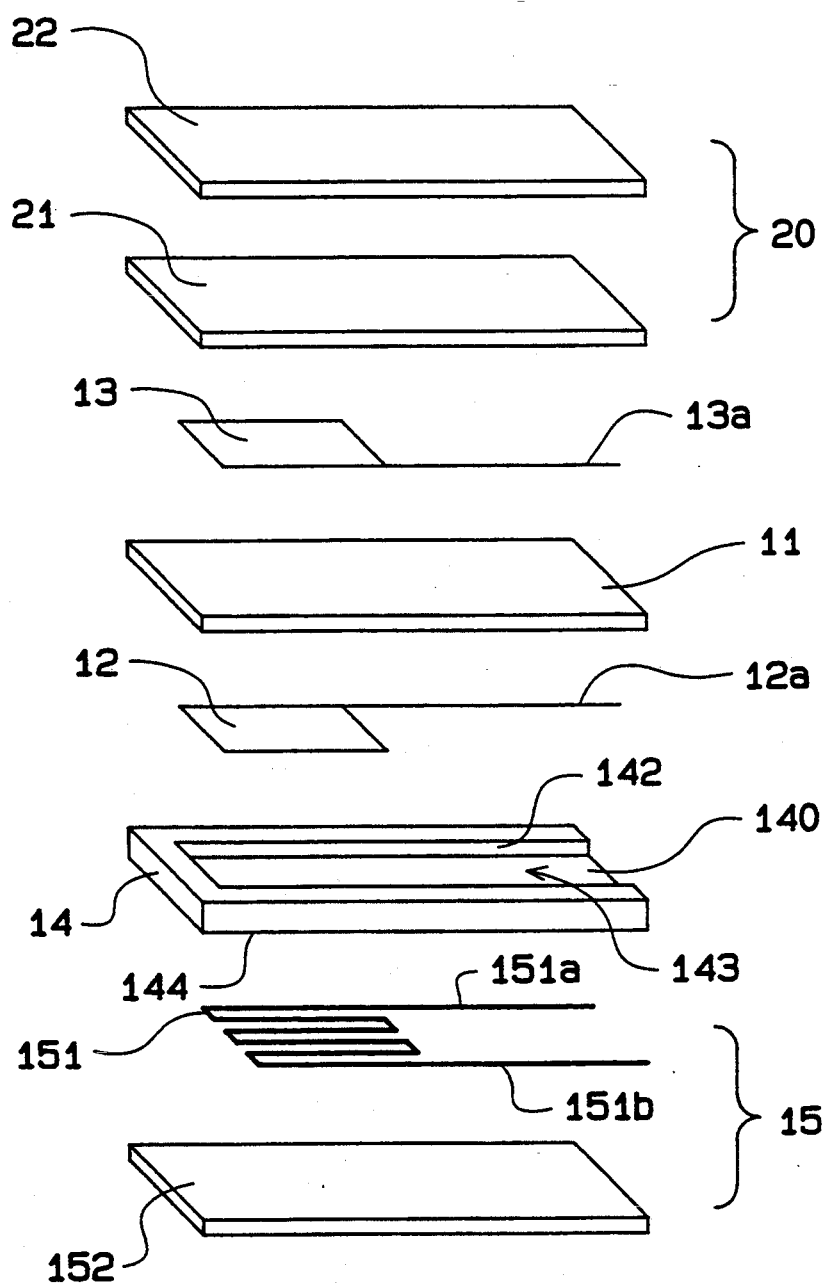
FIG. 2 is an exploded perspective view showing the cell (except for a protective layer) of FIG. 1.
Figure 4:
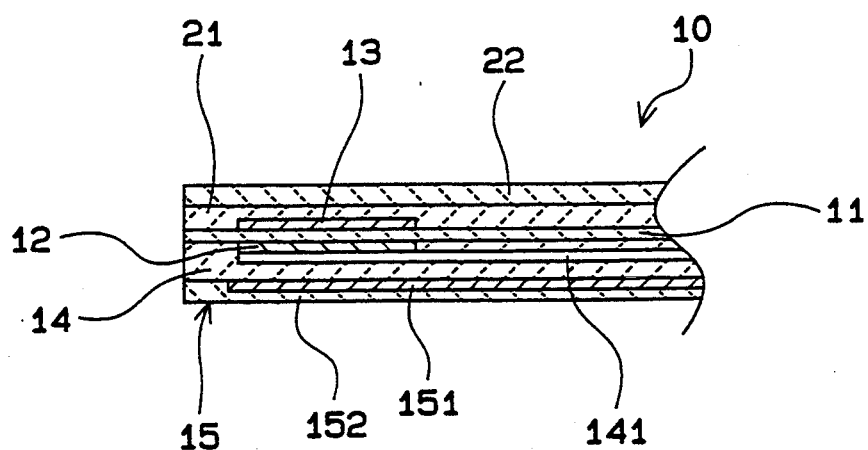
FIG. 4 is a longitudinal sectional view showing the cell according to the embodiment (except for the protective layer) taken along the line I—I of FIG. 1.

The solid electrolyte 11 of the cell 10 is a piece of sheet made of, for example, locally stabilized zirconia formed by a sheet forming method such as a doctor blade method or the like as shown in FIGS. 1, 2 and 4.

The porous reference electrode 12 and porous working electrode 13 made of platinum or the like are formed by a screen printing method or the like on both sides of the solid electrolyte 11 having a rectangular shape. Lead lines 13a and 12a are formed on the working electrode 13 and the reference electrode 12 by the screen printing method or the like in the same way.

It is possible to use the solid electrolyte 11 having a thickness in the range of about 50 $\mu$m to 300 $\mu$m, but it is preferable that the thickness be in the range of 100 $\mu$m to 200 $\mu$m (inclusive of the upper and lower limits) in view of the combination of the strength and the electric resistance of the sheet.

Also, it is possible to use the working electrode 13 and the reference electrode 12 having thicknesses in the range of from about 1 $\mu$m to about 20 $\mu$m, but it is preferable that their thicknesses be in the range of 5 $\mu$m to 10 $\mu$m (inclusive of the upper and lower limits) in view of the heat resistance and gas diffusion property.

The ambient air introduction duct 14 where a grooved portion 142 having a bottom 140 is formed, is produced by thermal bonding or the like, with the second surface 112 of the solid electrolyte 11 on which the reference electrode 12 is mounted. The air introduction duct 14 is in the form of a rectangular shape and is made of highly heat conductive ceramic such as alumina by an injection molding process or the like.

Also, the electric heater 15 is mounted on the opposite surface 144 of the ambient air introduction duct 14. The electric heater 15 is composed of a heating element 151, which generates heat by the electricity application of thereto, and a dielectric sheet 152 in the form of a rectangular shape for covering the heating element 151. Lead lines 151a and 151b are extracted from both ends of the heating element 151.

The rectangular gas permeation layer 21 and the rectangular gas shield layer 22 as well as the working electrode 13 are laminated in order on the first surface of the solid electrolyte 11.

The gas permeation layer 21 is a porous sheet for introducing the exhaust gas to the working electrode 13 and is formed of alumina, spinel, zirconia or the like by a sheet forming method or the like. Thereafter, the gas permeation layer 21 is integrally formed on the first layer 111 of the solid electrolyte 11 so as to cover the working electrode 13 by a bonding process such as thermal bonding. Alternatively, the gas permeation layer 21 may be integrally formed in the ceramic baking process by making ceramics such as alumina, spinel, zirconia or the like into a sheet and arranging it on the working electrode 13 and the solid electrolyte 11. Upon the formation of the gas permeation layer 21, the above-described ceramics may be formed on the first surface 111 of the solid electrolyte 11 by plasma welding.

The thickness d of the gas permeation layer 21 is in the range of from about 5 μm to about 300 μm, and the porosity is such that the average fine pore diameter is in the range of from about 40 Å to about 2000 Å. The porosity percentage is in the range of from about 2 to about 60%. The gas shield layer 22 is dense so as to suppress the permeation of the gas in the vertical direction relative to the surface of the working electrode 13. Upon the formation of the gas shield layer 22, the green sheet thereof is aligned in parallel with the working electrode 13 and thermally bonded on the surface of the gas permeation layer 21. Under this condition, the gas shield layer 22 is integrally baked. It is possible to form the gas shield layer 22 on the surface of gas permeation layer 21 by plasma welding.

It is possible to select material for the gas shield layer 22 from ceramics such as alumina, spinel, zirconia and the like. The thickness thereof is preferably in the range of from about 5 μm to about 300 μm. The average fine pore diameter is no more than 800 Å, and the porosity is preferably in the range of about 10% or less and is about 30% or less of the that of the gas permeation layer 21.

The heating element 151 of the electric heater 15 is formed by printing a paste made of a mixture of a platinum and heat resistant ceramics such as aluminum or the like on the dielectric sheet 152 made of alumina having a high purity by a screen printing method or the like. For example, the above-described shield layer 22, the gas permeation layer 21, both electrodes 12 and 13, the solid electrolyte 11, the ambient air introduction duct 14, and the electric heater 15 are laminated by a method such as a thermal bonding method. Then, these laminates are simultaneously baked to form the cell 10.

Furthermore, the outer layer that is brought into contact with the exhaust gas of the cell 10 is protected by the cover. The protective layer 16 is used to protect the clogging of the gas permeation layer 21 by the condensed components contained in the exhaust gas and an alumina having a large surface area is formed on the surface of the cell 10 by a dip method or a plasma welding method or the like. From the point of view of preventing the gas permeation layer 21 from clogging, it is sufficient that only the side faces of the gas permeation layer are covered by the protective layer 16. However, the overall surface of the cell 10 is covered by the protective layer 16 in order to enhance the temperature holding property of the cell 10 as a whole.

The porosity of the protective layer 16 is such that the average fine pore diameter is in the range of from about 100 Å to 2000 Å and the porosity percentage is in the range of from about 10% to about 70%.

Figure 5:
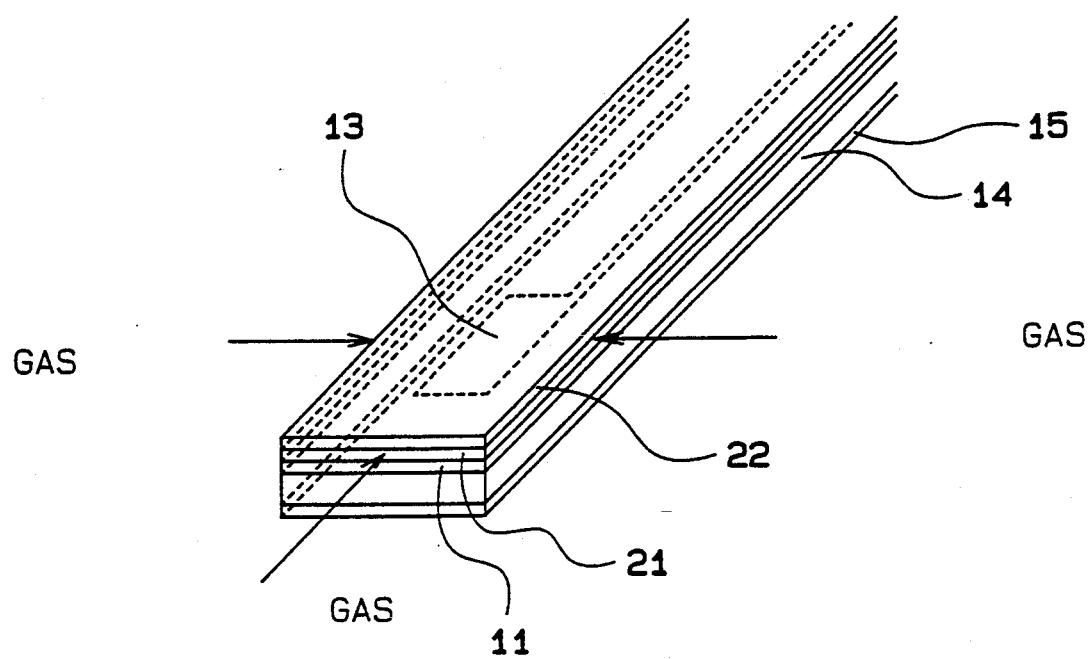
FIG. 5 is a perspective view showing the cell according to the embodiment.

FIG. 5 is a perspective view of the cell shown in FIG. 1. The gas to be measured is introduced into the gas permeation layer 21 of the gas diffusion resistance layer 20 from three directions. In FIG. 5, the depiction of the protective layer 16 shown in FIG. 1 is omitted.

The effect of the air fuel detecting apparatus 1 described above will be explained below.

In the cell 10 of the air fuel ratio detecting apparatus 1, the exhaust gas that will be introduced into the working electrode 13 is introduced from the side faces of the gas permeation layer 21, but is not introduced in the vertical direction of the gas permeation layer 21. Namely, since the surface of the gas permeation layer 21 is covered by the gas shield layer 22, the exhaust gas could not be 0 introduced in the vertical direction and is introduced into the interior of the permeation layer 21 from the side faces intersecting the vertical direction.

Figure 6:
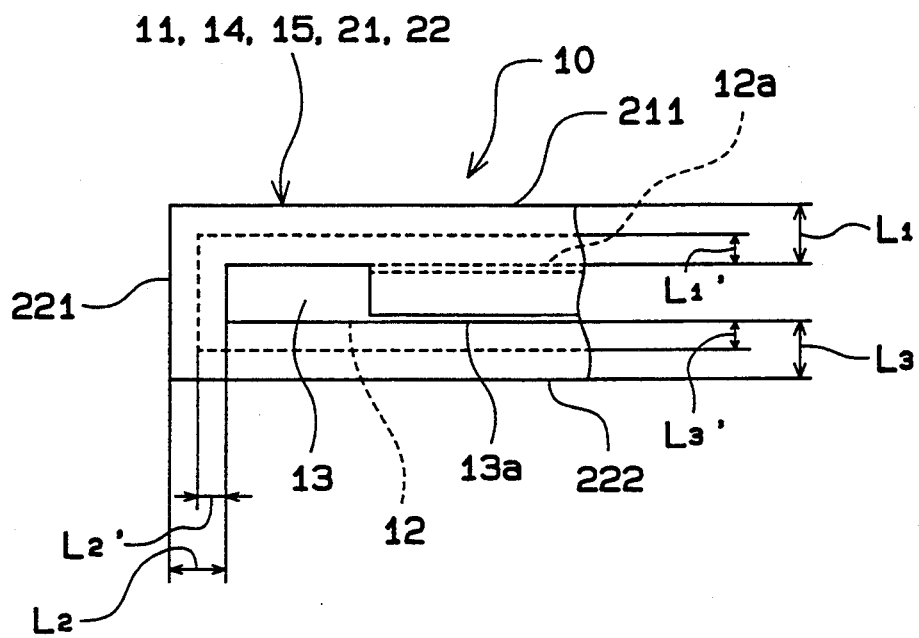
FIG. 6 is a plan view showing the cell of FIG. 4 illustrating the trimming.

On the other hand, the adjustment of the distance L (see FIG. 1) between the side faces of the gas permeation layer 21 through which the gas is to be introduced and the side faces of the working electrode 13 is very easy unlike the adjustment of the thickness of the gas permeation layer 21. More specifically, as shown in FIG. 6, the solid electrolyte 11, the ambient air introduction duct 14, the electric heater 15, the gas permeation layer 21, and the gas shield layer 22, which are constituents of the cell 10, are set and laminated, being substantially the same size or somewhat larger rectangular planar shape. The three-way side walls of components 211, 221 and 222 are cut so as to remove the unnecessary sheet sections up to the position indicated by the dotted lines in FIG. 6 by a laser trimming process or the like, so that the distances $L_1$, $L_2$, and $L_3$ may be adjusted to $L_1'$, $L_2'$, and $L_3'$. The three-way distances $L_1'$, $L_2'$, and $L_3'$ are set at the same distance so that the gas diffusion resistances are kept constant relative to the gas permeation layer 21 against the gas to be measured in any direction. It is natural, in this case, that the reference electrode 12 and the working electrode 13 face each other in the same position and have the same surface area.

Also, since it is possible to determine, as desired, the distance L with a higher degree of accuracy unlike the thickness of the gas permeation layer 21, it is possible to increase a diameter of the fine pores of the gas permeation layer 21. At the same time, the cell would be free from the adverse affect of changes in diameter of fine pores. This means that it is unnecessary to restrictively control the diameter of the fine pores.

The region corresponding to the distance L in the gas permeation layer 21 exhibits the diffusion resistance effect restricted by the oxygen contained in the gas to be measured and is set as a factor for determining this effect. Accordingly, the diffusion amount of the gas to be measured relative to the gas permeation layer 21 depends mainly on the above-described distance L. As a result, unlike the conventional structure, there is no difficulty during manufacturing in controlling the diameter of the fine pores of the resistance layer so as to be uniform. Furthermore, it is unnecessary to increase the thickness of the resistance layer for imparting the diffusion resistance effect when the gas to be measured is diffused in the vertical direction of the working electrode relative to the gas diffusion resistance layer, i.e., in the direction of the thickness of the resistance layer.

Figure 7:
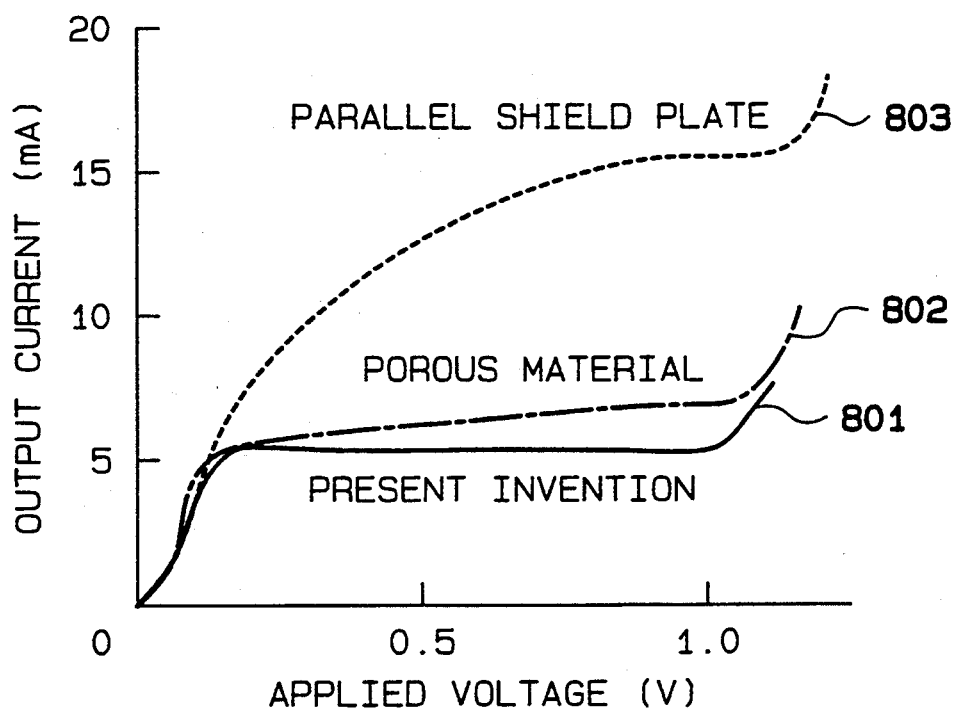
FIG. 7 is a graph showing an output current characteristic of the cell according to the present invention.

FIG. 7 shows a comparison of the structure of the present embodiment with the structures of the conventional cases. In FIG. 7, a curve 801 indicates the present invention, a curve 802 indicates the former conventional system, and a curve 803 indicates the latter conventional system. As will be understood from the comparison among the curves 801 to 803, according to the embodiment indicated by the curve 801, it is possible to obtain a clear limit current representative to substantially the same output current even though the application voltage may be widely changed. In contrast, in the curve 802 of the former conventional system, it is difficult to obtain a substantially constant output current relative to the applied voltage. Also, in the same way, according to the curve 803 of the latter conventional system, it is difficult to obtain a substantially constant output current relative to the applied voltage. In the latter conventional system, the output current may be kept substantially constant when the applied voltage exceeds slightly 1 V, but it is noted that this applied voltage is higher than the current applied voltage of about 0.2 V by which the output current may be kept substantially constant in the curve 801 of the present embodiment. Also, the width of the current applied voltage that generates a substantially constant output current is very narrow, and thus is difficult to control.

Figure 8:
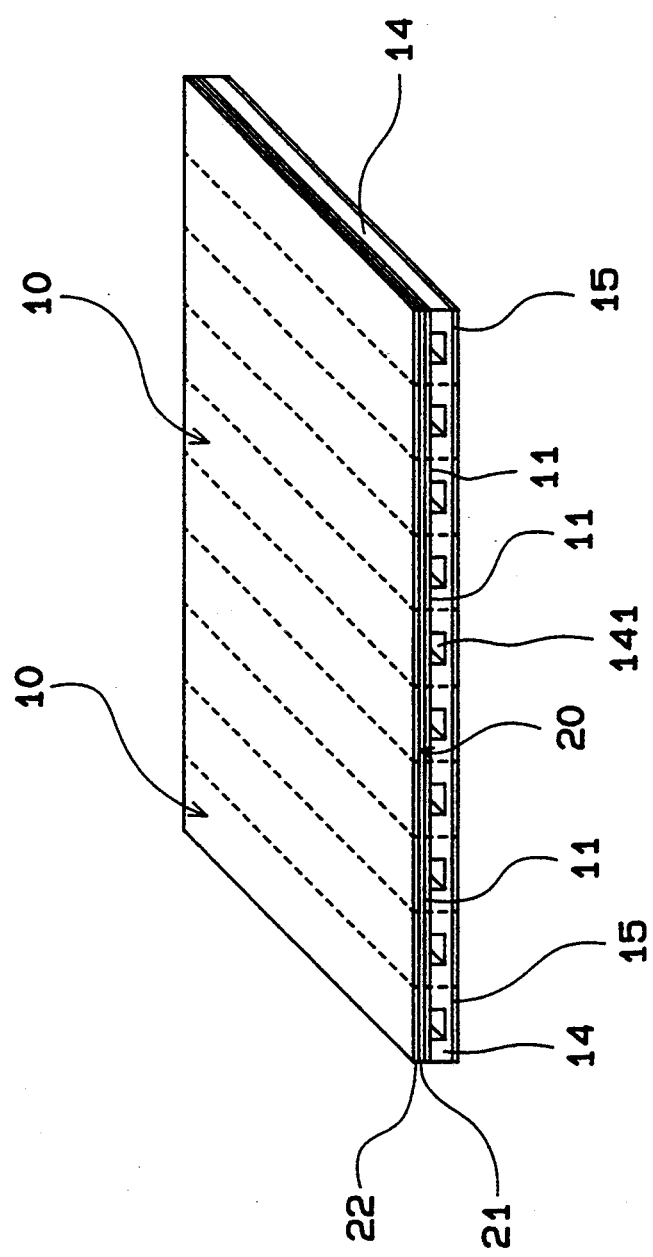
FIG. 8 is a perspective view showing a lamination process for the cell of the present invention.
Figure 9:
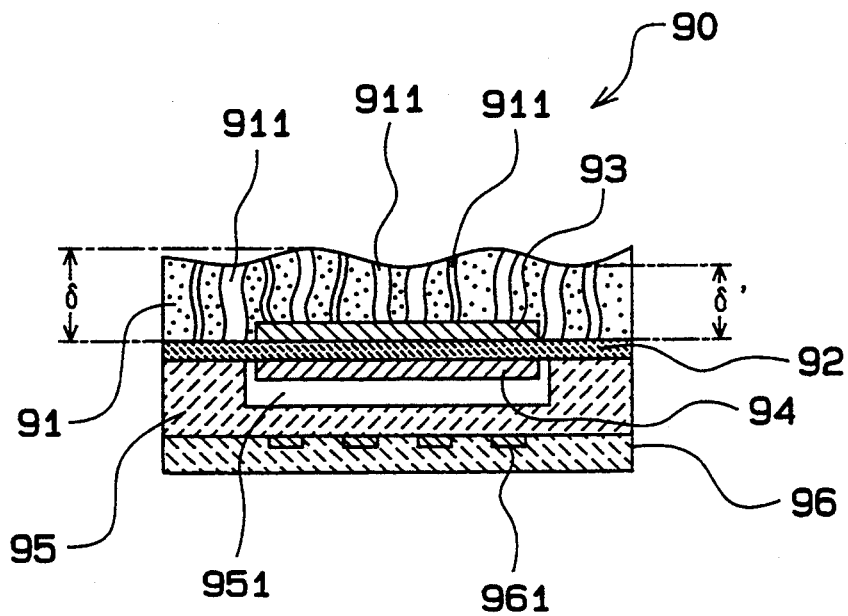
FIG. 9 is a cross-sectional view showing a cell of a conventional air fuel ratio detecting apparatus.
Figure 10:
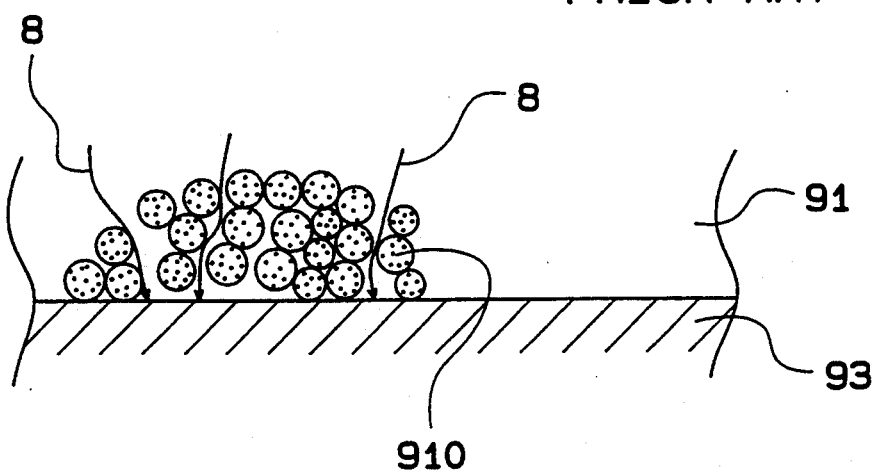
FIG. 10 is an illustration showing a gas diffusion resistance layer of the conventional cell.
Figure 11:
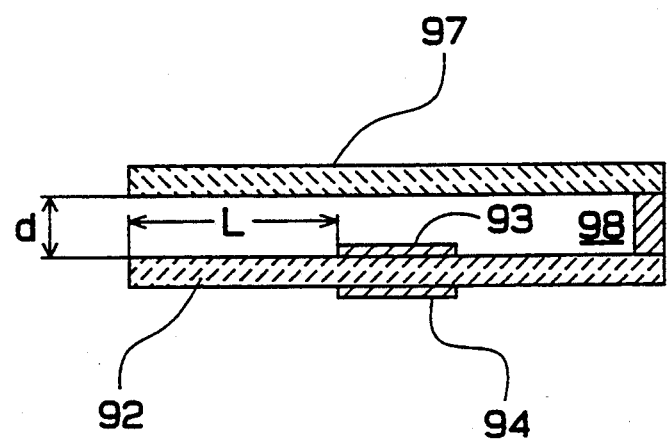
FIG. 11 is a cross-sectional view showing a cell of another conventional air fuel ratio detecting apparatus.

The cell 10 is integrally formed by laminating the respective components 11 to 15 and 20, and is baked simultaneously in a single process for integral formation. Also, it is possible to manufacture a large number of cells via a single process by forming a series of cells 10 using integral lamination of a series of respective components (11 to 15 and 20) as shown in FIG. 8. The cells may be divided before or after baking them. Accordingly, it is possible to mass produce a large number of cells with high efficiency at a low cost.

In particular, since the gas permeation layer 21 and the gas shield layer 22 may be baked at once from the green sheet in the baking process, it is possible to save manufacturing cost.

Also, since the protective layer 16 is provided on the cell 10, the gas permeation layer 21 is not easily clogged, thus allowing the gas permeation layer 21 to enjoy a long service life.

Also, since the working electrode 13 is not exposed directly to the exhaust gas, there is no fear of damage to the working electrode 13.

According to the present embodiment, as described above, it is possible to achieve a uniform and stable oxygen ion limit current and it is possible to provide an air fuel ratio detecting apparatus that may be easily mass produced at low cost.

In the foregoing embodiment, the solid electrolyte 11 is in the form of a plate, but it is of course possible to use a cylindrical tube into which the ambient air may be introduced.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. An air fuel ratio detecting apparatus comprising:
   a solid electrolyte having a first and second electrodes;
   a gas diffusion resistance layer having a diffusion resistance limited to oxygen contained in a gas to be measured, said gas diffusion resistance layer covering a surface and side faces of said first electrode and comprises a gas permeation layer and a gas shield layer;
   wherein said gas diffusion resistance layer is formed on said surfaces of said first electrode over an area from one of said side faces to a part of a surface of said solid electrolyte at a set distance;
   wherein the gas shield layer is formed on a surface of said gas permeation layer except for side faces thereof;
   wherein an area corresponding to said set distance between said side face of said gas diffusion resistance layer and said side face of said first electrode exhibits a diffusion resistance action limited to the oxygen in said gas; and
   wherein said gas shield layer forces said gas to reach said first electrode via an interior of said gas diffusion resistance layer from said side face of said gas diffusion resistance layer.

2. The apparatus according to claim 1, wherein a porosity of a part of said gas diffusion resistance layer through which said gas passes is in the range of from about 2 to about 60%.

3. The apparatus according to claim 2, wherein a thickness of said part having said porosity is in the range of from about 5 to 300 $\mu$m.

4. The apparatus according to claim 2, wherein the porosity of a part of said gas diffusion resistance layer, through which the gas to be measured is not to pass, is no more than 10%.

5. The apparatus according to claim 1, wherein said set distance between said side faces of said diffusion resistance layer and said side faces of said first electrode is kept constant over an entirety of said side faces of said diffusion resistance layer.

6. The apparatus according to claim 1, wherein said solid electrolyte is in the shape of plate wherein said first and second electrodes are located closer to one end of said solid electrolyte than to another end thereof; wherein said first electrode, covered by said gas diffusion resistance layer, has a first one end and a second end and side faces confronting each other, and has a rectangular shape, in plan view, smaller in area than said solid electrolyte; said gas diffusion resistance layer is formed to extend up to said first one end and said confronting side faces of said solid electrolyte; and distances between three side faces of said gas diffusion resistance layer corresponding to said first one end and said confronting side faces of said solid electrolyte and said first one end and said confronting side faces of said first one of said electrodes are kept constant.

7. The apparatus according to claim 1, wherein a periphery of the side face, of said diffusion resistance layer through which at least gas to be measured enters, is covered by a porous protective layer.

8. An air fuel ratio detecting apparatus comprising:
   a solid electrolyte in the shape of a plate having a first surface exposed in gas to be measured and a second surface exposed in ambient air;
   a working electrode formed on said first surface of said solid electrolyte;
   a reference electrode formed on said second surface of said solid electrolyte;
   an ambient air duct arranged on said second surface of said solid electrolyte for exposing said reference electrode to the ambient air;
   an electric heater arranged opposite to said second surface of said solid electrolyte; and
   a gas diffusion resistance layer formed on said first surface of said solid electrolyte for covering a surface and side faces of said working electrode, with a surface portion of said gas diffusion resistance layer which is formed of dense material that prevents the gas to be measured from entering in a vertical direction of said working electrode but allows the gas to be measured to enter from the side faces perpendicular to said vertical direction;

wherein a distance between the side faces of said gas diffusion resistance layer and the side faces of said working electrode is set as a factor for determining a diffusion resistance limited to oxygen contained in the gas to be measured.

9. The apparatus according to claim 8, wherein said gas diffusion resistance layer consists of a porous gas permeable ceramic sheet and a dense gas shield ceramic sheet which are both laminated and baked.

10. The apparatus according to claim 8, wherein a periphery of the side face, of said diffusion resistance layer through which at least gas to be measured enters, is covered by a porous protective layer.

11. A method for manufacturing an air fuel ratio detecting apparatus, comprising the following steps of:
   printing first and second electrodes on surfaces of a solid electrolyte sheet;
   laminating, on one surface of said solid electrolyte sheet, a porous gas permeable ceramic sheet as well as on one surface of said first and second electrodes;
   laminating a dense gas shield ceramic sheet on the surface of said gas permeation ceramic sheet; and
   forming the gas diffusion layer having no permeation characteristic to the gas at its surface, on the surface of said solid electrolyte including the surface of one of said first and second electrodes through a baking process.

12. A method for manufacturing an air fuel ratio detecting apparatus comprising the following steps of:
   providing a solid electrolyte sheet having a working electrode formed on a first surface on a side of gas to be measured, as a top surface, and a reference electrode formed on a second surface on a side of ambient air, said first and second electrodes confronting each other and having a same projection area, a porous gas permeation ceramic sheet being laminated on said working electrode of said solid electrolyte sheet, and a dense gas shield ceramic sheet being laminated on said porous gas permeation type ceramic sheet;
   forming said solid electrolyte sheet, said gas permeation ceramic sheet and said gas shield ceramic sheet in the same planar shape; and
   under a lamination condition of said solid electrolyte sheet, said gas permeation ceramic sheet and said gas shield ceramic sheet, removing unnecessary parts by trimming said solid electrolyte sheet, said gas permeation ceramic sheet and said gas shield ceramic sheet so that a distance is formed between each of the side faces of said working electrode and said reference electrode and;
   maintaining a constant distance between each of said solid electrolyte sheet, said gas permeation ceramic sheet, and said gas shield ceramic sheet.

* * * * *